United States Patent [19]
Loisel

[11] Patent Number: 5,465,610
[45] Date of Patent: Nov. 14, 1995

[54] DEVICE FOR THE CHARACTERIZATION OF THE FOAMING PROPERTIES OF A PRODUCT WHICH IS AT LEAST PARTIALLY SOLUABLE

[75] Inventor: William G. Loisel, Nantes, France

[73] Assignee: Institut National de La Recherche Agronomique, France

[21] Appl. No.: 162,061

[22] PCT Filed: Jun. 5, 1992

[86] PCT No.: PCT/FR92/00509

§ 371 Date: Dec. 7, 1993

§ 102(e) Date: Dec. 7, 1993

[87] PCT Pub. No.: WO92/22799

PCT Pub. Date: Dec. 23, 1992

[30] Foreign Application Priority Data

Jun. 11, 1991 [FR] France .................... 9107269

[51] Int. Cl.⁶ .................................................. G01N 13/00
[52] U.S. Cl. ....................... 73/60.11; 73/291; 73/304 R; 356/440
[58] Field of Search ............... 73/60.11, 61.41, 73/61.43, 291, 304 R; 324/439, 450; 356/427, 440; 340/620

[56] References Cited

U.S. PATENT DOCUMENTS

| | | | |
|---|---|---|---|
| 1,866,296 | 7/1932 | Christmann | 73/60.11 |
| 3,151,061 | 9/1964 | Orr | 208/328 |
| 3,498,131 | 3/1970 | Rickey | 340/620 |
| 5,003,488 | 3/1991 | Hardy | 364/509 |

FOREIGN PATENT DOCUMENTS

| | | |
|---|---|---|
| 0252738 | 1/1988 | European Pat. Off. . |
| 1476857 | 3/1967 | France . |
| 2551260 | 5/1977 | Germany . |
| 4036048 | 5/1991 | Germany ............. 73/60.11 |
| 2158574 | 11/1985 | United Kingdom . |

OTHER PUBLICATIONS

Kato et al., "Determination of foaming Properties . . .", Journal of Food Science, vol. 48, pp. 62–65, 1983.
Copy of European Search Report (1 page).

*Primary Examiner*—Hezron E. Williams
*Assistant Examiner*—Michael J. Brock
*Attorney, Agent, or Firm*—Bierman and Muserlian

[57] ABSTRACT

A device for the characterization of the foaming properties of a product at least partially soluble in a liquid comprising a transparent analysis column (1) provided at its base with a porous allowing filter (2) to homogeneously introduce a gas flow through the column to effect foaming of the product (3) located at the base of the analysis column (1) characterized in that it further comprises an automatic measuring system (28) to determine the foam height in column (1), an automatic measuring system (24, 24', 25) to determine the volume of product (3) to form the foam, means to visualize and/or to process the measured data and a pressure compensation system to avoid drainage and percolation of product (3) through filter (2) when gas injection is stopped.

8 Claims, 2 Drawing Sheets

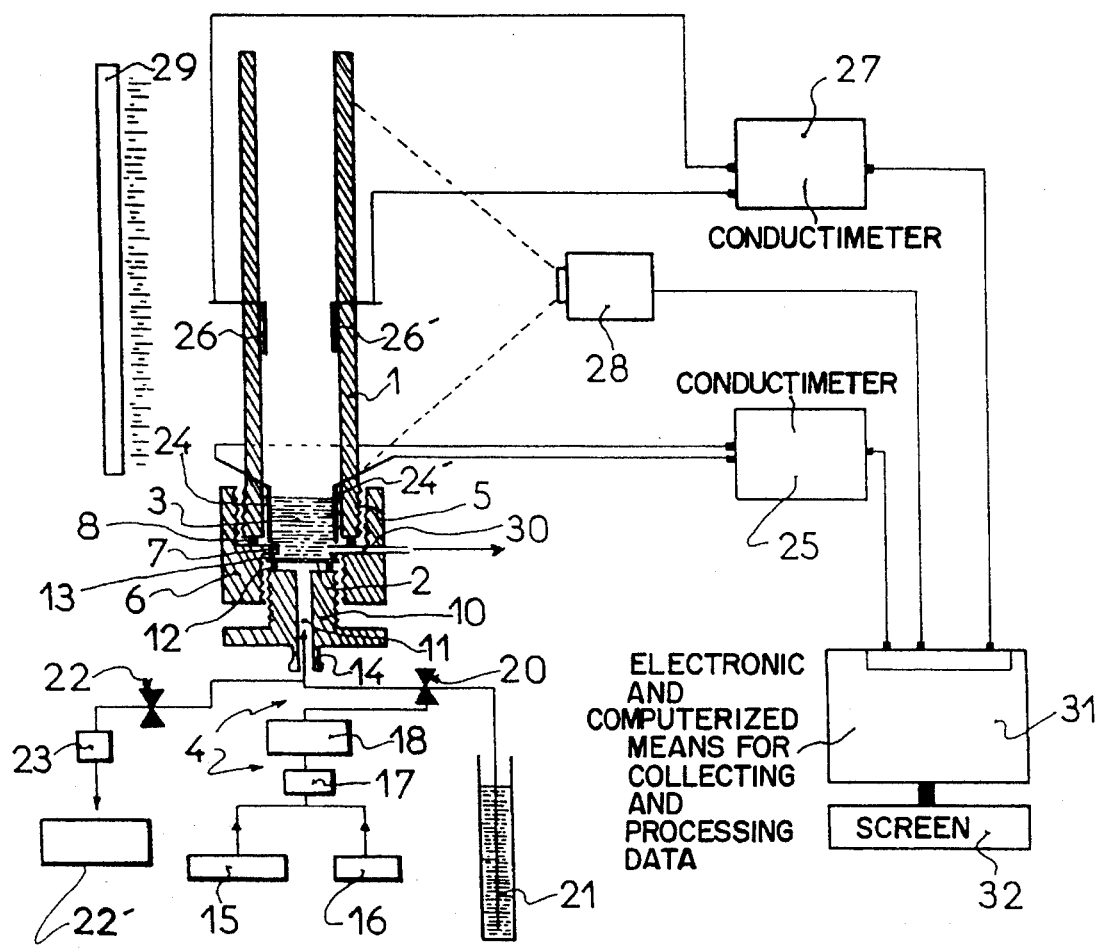
_fig.1_

DEVICE FOR THE CHARACTERIZATION OF THE FOAMING PROPERTIES OF A PRODUCT WHICH IS AT LEAST PARTIALLY SOLUABLE

STATE OF THE ART

This invention relates to a device able to characterize the foaming properties (foaming capacity and stability of the foam) of products in solution or in suspension.

In the fields of cosmetology or of the farm-produce industry especially, the purpose is to determine as accurately as possible the foaming properties of certain products designed to be introduced into various preparations, related to foodstuffs or not, characterized by an air-containing texture or a mellow texture, such as soaps, shampoos, liver foams . . . . Starting from a suspension or a solution of the product to be tested, a foam is characterized by its formation and degradation conditions; the foaming properties are thus determined by three factors, i.e.:

the formation kinetics of the foam, the foaming capacity, which corresponds to the measure of the volume of foam available after introduction of a preset quantity of gas into the solution and the foam stability, which corresponds to the time-related decrease in volume of the foam.

The visual methods to determine and to measure these factors, by assessing the foam volume, are not entirely satisfactory because, on the one hand, these measures are relatively inaccurate and, on the other, because this type of measure does not reflect the qualitative factors of the foams such as the thickness of the walls or the size of the bubbles.

Moreover, various factors such as the concentration, the pH-acidity, the temperature and the production methods of the foam affect the foaming properties of the products in solution or in suspension.

Taking into account the eagerness, as well with the industrialists as with the research laboratories, to have standardized procedures to measure the foaming properties of proteins, especially, one has endeavoured to assess the foaming properties by measuring the physical constants decisive for the characteristics of the foams.

It has been shown that these characteristics could almost be obtained by measuring the conductivity of the foams (Journal of Food Science-Volume 48, 1983 pages 62 to 65). This article describes a device enabling to characterize the foaming properties of products which are at least partially soluble, on the basis of the conductivity measure of the foam formed. The device consists of a glass column, arranged vertically and sealed, at its base, by a glass filter on which the solution to be analysed has been placed. A gas inlet connected to the lower section of the column enables to generates a gas flow through the glass filter in order to cause the solution to foam. A conductivity measuring cell is located on the column in order to determine the conductivity of the foam formed.

The studies carried out on the basis of this device show a strong correlation between the initial conductivity of the foams and the foaming capacity (foaming capacity=f(Ci)), as well as between this conductivity and the stability of the foam (foam stability=f $(Co \times \Delta t/\Delta C)$) where:

$\Delta C$=change in conductivity $\Delta t$=time interval $C_o$=conductivity at t=0, obtained by extrapolation of the second part of the C=f(t) curve.

This type of measure enables to note differences in foaming properties which cannot be detected by the sole change in volume of the foam. However, this type of measure underlines the foaming properties of the product analysed only indirectly, with all the risks of errors associated with the correlation system. Besides, even if it enables to standardize the determination of the foaming properties by stringent constraints, this apparatus is limited as regards the panel of characteristics which can be derived from the foam undergoing formation or degradation. Moreover, the measure relates to a fraction of the foam only.

The purpose of this invention is to remedy these defects while suggesting a characterization device of the foaming properties of products in solution or in suspension, liable to measure automatically a whole range of characteristics of the foams in order to accurate the characterization of the foaming properties of the product analysed.

The absolute measures derived from the foam, already formed or during degradation, enable to characterize partially the foaming properties of the product tested; besides, on the basis of these absolute values, it is possible to extract calculated measures to accurate the characterization and to define more accurately the qualitative and quantitative aspects of the foams.

SUMMARY OF THE INVENTION

The invention relates to a device for the characterization of the foaming properties of a product which is at least partially soluble, of the type described above, i.e. containing a transparent analysis column, whose base is fitted with a means in the form of a porous filter, for instance, which enables the introduction of a gas flow and its homogeneous distribution in order to cause the solution placed on the bottom of the analysis column to foam. According to the invention, the device comprises an automatic measuring system of the height of the foam formed in the column and an automatic measuring system of the volume of solution used in order to obtain this foam. On the basis of the measure of the volume of foam and of the volume of liquid in the foam, the physical density of the foam can be calculated quite simply (volume of foam/volume of liquid ratio); this calculation is preferably carried out automatically.

Measuring the height of the foam is advantageously performed using a linear camera arranged opposite the analysis column. This camera may, moreover, be used simultaneously to measure the opacity of the foam.

The system of measure for the volume of solution used to form the foam consists advantageously of a pair of electrodes, for instance in platinum, arranged at the bottom of the column and connected to a conductimeter.

According to another characteristic of the device, the analysis column comprises, in its lower section, a valve-shaped means of distribution of the gas flow. Closing this valve enables to inject gas through the filter and opening the valve connects to a device in the form of a column of liquid which enables to provide a back pressure through the filter which avoids percolation and drainage of the solution. The height of the column of liquid is adjusted in relation to the back pressure desired.

According to another characteristic of the invention, the device comprises a system to measure the quantity of gas injected. One can also add a system to measure the foam conductivity, consisting of one or several pairs of electrodes arranged along the height of the column and connected with a conductimeter.

According to an additional characteristic, the device comprises a hole, arranged just above the filtering means, designed for purging and cleaning the column.

Moreover according to the invention, the device comprises computerized means which provide the automatic control of the system, the viewing of raw data and the processing of this data in order to obtain additional parameters.

BRIEF DESCRIPTION OF THE DRAWINGS

The invention is illustrated, without being limited, by the following description of a particular embodiment, given for exemplification purposes and represented on the appended drawings in which:

FIG. 1 shows diagrammatically the whole device according to the invention;

DETAILED DESCRIPTION OF THE INVENTION

Figure 2:
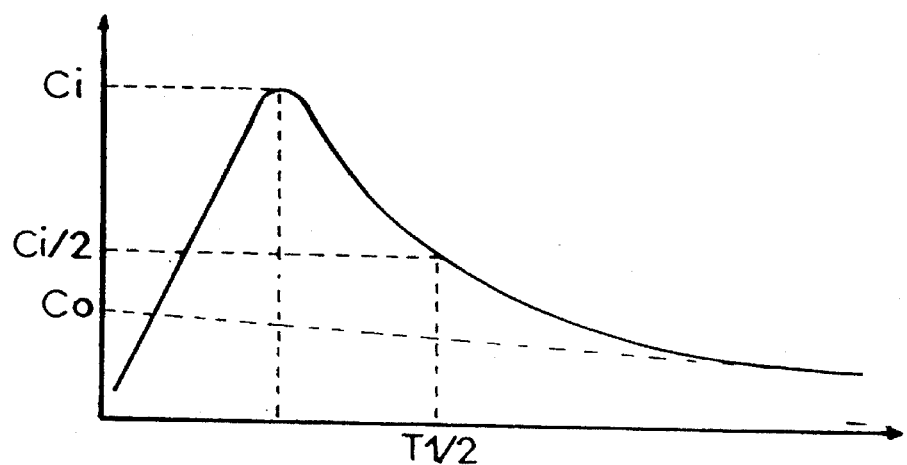
FIGS. 2 and 3 show resulting curves liable to be obtained by the device of FIG. 1.

As represented on the drawing of FIG. 1, the device according to the invention comprises of an analysis column 1, arranged vertically, whose base is fitted with a filter 2. The filter 2 seals the bottom of the column 1 to partition the product 3 to be analysed, which is in the form of a solution or of a suspension. The filter 2 also enables the flowing of a gas whose distribution circuit 4 is connected to the lower part of the column. The flow of the gas through the filter 2 is designed for causing the solution 3 of the product to be analysed, to foam.

The column 1 is associated with a set of sensors which allow measuring various parameters which will be detailed below.

The analysis column 1 consists of a glass cylinder or of a translucent plastic material; it is arranged vertically and comprises, at its base, an external thread 5 which enables to screw it onto a more or less cylindrical reception base 6. The base 6 comprises an internal collar 7 onto which the said column 1 rests via an annular gasket 8.

An additional body 10 drilled in its centre 11 to maintain the filtering means 2 in position, is screwed on the lower part of the base 6. The filtering means can be made of sintered glass or any other system with a determined porosity, selected with respect to its porosity. The sintered element 2 is mounted between the blocking unit 10 and the collar 7 of the base 6 via annular gaskets 12 and 13 arranged for tightness purposes. The base of the additional unit 10 comprises a circular stub 14 designed for the connection of the distribution circuit 4 of the gas flow.

The gas used depends on the product that one wants to analyse; it may consist of a flow of air, nitrogen, carbon gas or any other gas, obtained from a compressor 15 or a storage bottle 16. In both cases, the original gas flow is controlled by a pressure gauge 17 and goes through a flow meter 18 which enables measuring the volume of gas delivered. The sintered element 2 which seals the base of the column 1 enables homogeneous distribution of the gas flow arriving through inlet 11 in order to cause the product 3 to foam.

A squeeze solenoid valve 20 controls the distribution of the gas flow. In closed position, it authorises injection of the gas through the sintered element 2 into the analysis column 1; in open position, the gas flow is stopped. When the solenoid valve 20 is in this open position, in order to stop the production of foam in the column, one should advantageously provide a pressure compensation system which allows to guarantee the absence of drainage and percolation under the said column 1, through the sintered element 2. The compensation system is obtained by connecting the distribution circuit 4, via the solenoid valve 20, to a column of liquid 21. The height of this column 21 enables to adjust the back pressure required, at the level of the sintered element 2.

Moreover, under the effect of a manual valve 22, the product 3 can be sucked out of the column 1 in order to be discharged into a basin 22', for instance. This suction phenomenon is advantageously caused by water flowing through a Venturi tube 23 (liquid jet vacuum pump) thus creating a depression.

The distribution circuit, consisting of a plastic pipework, must be reduced as much as possible between the various units in order to avoid all disturbances (loss of weight, leakage . . . ).

The analysis column 1 comprises at its base a pair of platinum electrodes 24, 24', connected to a conductimeter 25. The electrodes 24, 24' are used as probes and are arranged so that the processing of the information delivered enables to assess the volume of liquid present at the bottom of the column.

A second pair of platinum electrodes 26, 26' is arranged more or less in the middle of the column 1, above the level of the starting solution. This pair of electrodes 26, 26' enables to measure the conductivity of the foam thus formed; it is connected to a conductimeter 27.

In order to have different test points, several other couples of electrodes, identical to those 26, 26' described above, can be arranged along the height of the column.

The height of foam formed is determined by one or several photoelectric cells, one or several level sensors or, preferably, by a linear camera 28.

This linear camera 28 is located opposite the column 1 in order to enable measuring and automatic tracking of the height of foam formed. This measure is performed by the classical means related to this type of material; the reading contrast has been advantageously improved by fitting the analysis column 1 between the camera 28 and a light source 29. Taking into account the diameter of the column 1, the measure of the foam height enables to deduct, after processing, the formation speed of the foam and the volume of foam formed in said column.

It should be noted that the base 6 can be modified to allow use of the transparent columns 1 of a different diameter; the camera 28 can then be advantageously positioned on calibrated marks which enable to determine various foam heights in relation to the column used.

In addition of the measure of the foam height, the camera 28 can advantageously be adapted and adjusted to suit the measuring of the optical density of said foam.

The base 6 also comprises a sealable hole 30, arranged in the collar 7, just above the level of the sintered element 2. This hole 30 enables cleaning the device by sucking the rinsing liquid above and through the sintered element 2.

The three types of sensors: electrodes 24, 24', electrodes 26, 26' and camera 28 enable to obtain raw absolute measures which characterize the foaming properties of the product 3; these various measures are collected and processed by electronic and computerized means 31, then displayed on a screen 32; the whole is managed by an appropriate software.

The evolution of the volume of liquid monitored by measuring the conductivity at the level of the electrodes 24, 24' enables to measure the volume of liquid present in the foam formed.

The height of foam detected by the camera 28 enables to obtain and to monitor the volume of foam formed.

The opacity of the column 1, also detected by the camera 28, enables moreover to determine the "optical density" (OD) of the foam.

Moreover, and as it can already be done, the couple of electrodes 26, 26' enables to measure and to monitor the conductivity of this foam with the elapsed time.

Storage in memory and computerization of these various time-related parameters enable to deduct automatically a whole set of very accurate characteristics whose some examples will be defined in relation to the analysis process.

Preparing the material consists in applying voltage to all the devices and in cleaning and rinsing the analysis column.

After checking and adjusting the gas rate, a preset quantity of the product 3 is poured into the column 1. The solenoid valve 20 is open; the column of liquid 21 exerts permanently a back pressure on the sintered element 2 which prevents the liquid 3 from falling into the gas distribution duct 11.

The electronic and computerized system is adjusted in relation to the variable parameters of the device: especially the diameter of the column 1 as well as the determination of the gas injection shut-down mode (in relation to time, volume of foam obtained, volume of liquid used or change in slope of one of the curves obtained . . . ).

Once the solution to be analysed has been injected into the column, one should wait for approximately 30 seconds for the solution to be stabilized. Computer display of the volume of liquid present, determined by the pair of electrodes 24, 24', is then matched with the actual quantity poured by the user. This adjustment is performed whatever the conductivity of the product to be analysed.

Initialisation of the system is performed at t=0.

The measuring sequence starts as soon as the solenoid valve 20 has been closed. This closing causes the chosen gas (air, nitrogen, inert gas . . . ) to be injected into the column 1 and consequently, the bubbling through and the formation of foam above the product 3 in solution or in suspension.

Stopping the injection of gas using the solenoid valve 20 depends on the parameter chosen: time, volume of liquid, volume of foam, loss of conductivity of the foam, volume of air injected . . . .

The measures taken by the computerized and electronic system 31 via the conductimeters 25 and 27 as well as the camera 28, are for instance performed every two seconds starting from t=0, for 30 to 45 minutes. These measures enable, at first, to determine the conditions of formation of the foam and, then, its conditions of degradation. The analysis can be stopped in relation to the time elapsed, the volume of liquid used, the volume of foam remaining, the minimum conductivity of the foam or quite simply by depressing a stop key.

Thanks to the various sensors 18, 24-24', 26-26' and 28, the device according to the invention measures the following parameters: time, quantity of liquid used, conductivity of the foam, volume of foam, gas flow rate and "optical density" of the foam.

These are absolute values directly linked to the measured parameters: as such they specify properties of the foam obtained and can also be processed by the computer means to characterize more accurately still the formation and degradation properties of the foam, either punctually or with the elapsed time.

The computer means can for instance enable to measure the following:

physical density of the foam, which corresponds to the volume of foam/volume of liquid used ratio;

foaming quality: volume of foam/volume of gas;

volume swell: variation of the volume of foam/variation of the volume of gas;

transparence: function of the camera signal;

homogeneousness: function of the conductivity of the foam.

One can also note that the measure of conductance of the foam is related to its density; indeed, the denser the foam, the higher the conductance: the density of the foam being defined according to the size of the bubbles with respect to the quantity of liquid necessary to its formation.

Processing the parameters measured can also enable to obtain characterization of the drainage and coalescence kinetics, which account for the degradation properties of the foams.

One can also conduct time-related monitoring of the volume of the foam and of its optical characteristics or perform an analysis of the specific values of a given product:

maximum adsorption of liquid, maximum conductivity of the foam, foaming capacity by measuring the difference between the gas injected and the volume of foam.

All these parameters (non exhaustive list) enable to characterize the structure and the stability of the foam.

Computer processing enables, on the basis of the measures, to obtain during the experimentation period, various types of curves such as: the quantity of liquid in the foam, the level of liquid, the volume of foam, the conductivity, their transforms, logarithm or exponential, variations of their slopes, smoothing the experimental curves, regressions that can be derived, etc . . . .

FIG. 2 represents a possible example of a curve showing the conductivity of a foam in relation to time.

This curve enables to determine:

the foaming capacity: Ci the stability of the foam: t ½ corresponding to Ci/2 the index of stability: Co×($\Delta T/\Delta C$)

Figure 3:
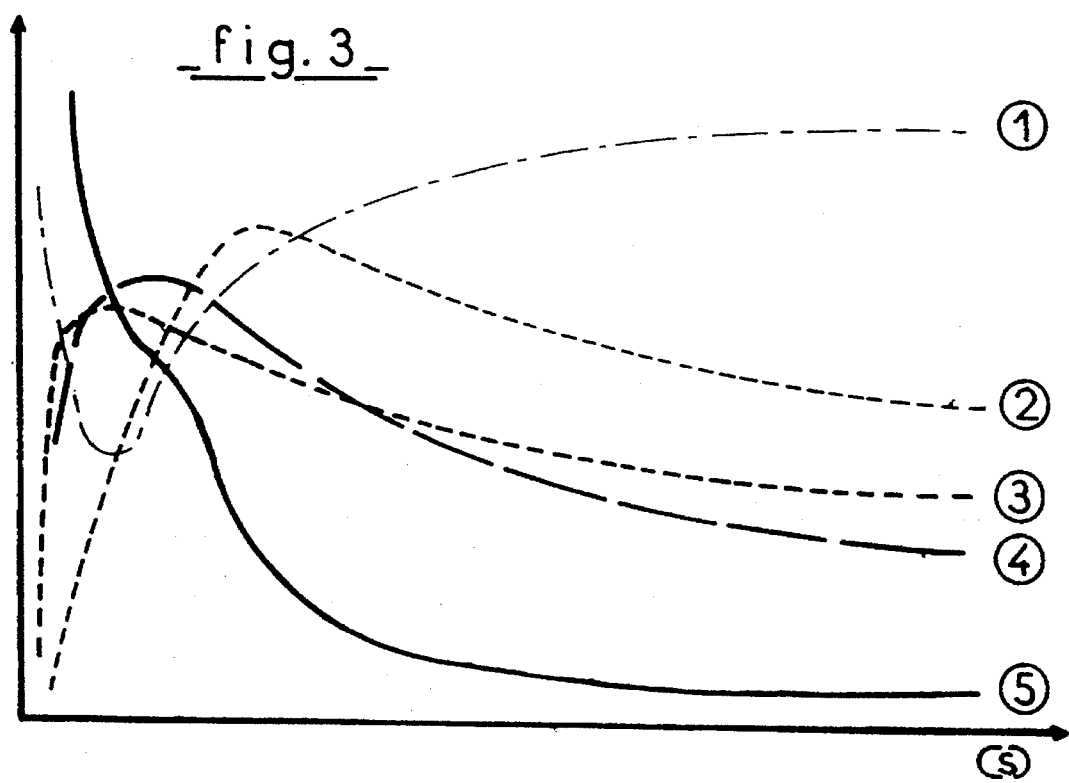

FIG. 3 represents various examples of curves that can be obtained with the device according to the invention:

Curve 1: kinetics of the liquid in the column,

Curve 2: evolution of the volume of foam,

Curve 3: log of the liquid in the foam,

Curve 4: log of the conductivity in the foam,

Curve 5: density of the foam.

The device according to the invention enables to measure a whole range of values accounting completely for the foaming properties of products in solution or in suspension.

Automatic tracking enables to choose quite accurately the systems which control the formation of the foam: time, volume, liquid, change in slope . . .

This system is very general-purpose as regards the volume of liquid used (depending on the geometry of the foam cells); it enables using solution volumes comprised between 5 and 25 ml.

This type of device finds a particularly interesting application in the field of cosmetology or farm-produce industry, for instance to determine the foaming characteristics of proteins. Any research and development laboratory can use it in order to characterize raw materials and finished products.

The sole purpose of the reference signs placed after the technical characteristics mentioned in the claims is to facilitate the understanding of the said characteristics, without limiting their scope whatsoever.

I claim:

1. A device for the characterization of the foaming properties of a product at least partially soluble in a liquid comprising a transparent analysis column provided at its base with a porous filter to allow homogeneously introduction of a gas flow through the column to effect foaming of the product located at the base of the analysis column characterized in that it further comprises an automatic measuring system for determining the foam height in the column, an automatic measuring system for determining the volume of product to form the foam, means for visualizing and/or processing the measured data of these measuring systems, and a gas flow distribution system wherein the gas flow is distributed by a valve whose closing effects gas injection through the filter and whose opening effects connection with a device with a liquid column to provide back pressure through the filter to avoid drainage and percolation of product through the filter.

2. The device of claim 1 wherein the measuring system of the foam height is a linear camera.

3. The device of claim 1 wherein the volume measuring system is a pair of electrodes arranged at the base of the column and connected to a conductimeter.

4. The device of claim 1 provided with a measuring system to determine the amount of injected gas.

5. The device of claim 1 wherein the foam measuring device is an opacity measuring system.

6. The device of claim 1 provided with a foam conductivity measuring system comprising at least two electrodes arranged along the height of the column and connected to a conductimeter.

7. The device of claim 1 wherein the column is provided with a hole immediately above filter for draining and cleaning.

8. The device of claim 1 provided with a computerized means for automatically monitoring of the apparatus, viewing raw data and processing same.

* * * * *